United States Patent
Michael et al.

(10) Patent No.: US 8,541,377 B2
(45) Date of Patent: Sep. 24, 2013

(54) OPTIMIZED DENGUE VIRUS ENTRY INHIBITORY PEPTIDE (DN81)

(75) Inventors: Scott F. Michael, Estero, FL (US); Sharon Isern, Estero, FL (US); Robert Garry, New Orleans, LA (US); Ram Samudrala, Mukilteo, WA (US); Joshua Costin, Naples, FL (US); Ekachai Jenwitheesuk, Ratchaburi (TH)

(73) Assignee: Florida Gulf Coast University, Fort Myers, FL (US)

( * ) Notice: Subject to any disclaimer, the term of this patent is extended or adjusted under 35 U.S.C. 154(b) by 590 days.

(21) Appl. No.: 12/668,828

(22) PCT Filed: Jul. 11, 2008

(86) PCT No.: PCT/US2008/069716
§ 371 (c)(1),
(2), (4) Date: Nov. 29, 2010

(87) PCT Pub. No.: WO2009/048658
PCT Pub. Date: Apr. 16, 2009

(65) Prior Publication Data
US 2011/0112031 A1    May 12, 2011

Related U.S. Application Data

(60) Provisional application No. 60/949,710, filed on Jul. 13, 2007.

(51) Int. Cl.
*A61K 38/16* (2006.01)
*A61K 39/12* (2006.01)
*A61P 31/12* (2006.01)

(52) U.S. Cl.
USPC ......... 514/21.3; 514/3.7; 530/324; 424/218.1

(58) Field of Classification Search
None
See application file for complete search history.

(56) References Cited

PUBLICATIONS

Hrobowski, 2005, Virology Journal, 2, 49.*

* cited by examiner

*Primary Examiner* — Satyanarayana R Gudibande
(74) *Attorney, Agent, or Firm* — Robert Varkonyi; Smith & Hopen, PA (57) ABSTRACT

The invention relates peptide entry inhibitors and methods of determining such inhibitors that are bindable to regions of viruses having class II E proteins, such as the dengue virus E protein, as candidates for in vivo anti-viral compounds.

13 Claims, 4 Drawing Sheets

| C | prM | E | NS1 | NS2A | NS2B | NS3 | ns4a | ns4b | NS5 |

Dengue Virus Genomic Organization

OPTIMIZED DENGUE VIRUS ENTRY INHIBITORY PEPTIDE (DN81)

CROSS-REFERENCE TO RELATED APPLICATION

This is a national stage application of PCT/US2008/69716, filed Jul. 11, 2008, to which this application claims priority from and any other benefit of U.S. provisional patent application Ser. No. 60/949,710 filed Jul. 13, 2007, which is incorporated herein by reference.

GOVERNMENT SUPPORT

The U.S. Government has a paid-up license in this invention and the right in limited circumstances to require the patent owner to license others on reasonable terms as provided for by the terms of grant no. GM068152 awarded by the National Institute of Health (NIH).

The invention relates to inhibitors that are bindable to regions of a virus. More particularly, the invention relates to inhibitors that are bindable to regions in the dengue virus envelope glycoprotein, or dengue virus E protein, which is a class II viral E protein. Even more particularly, the invention relates to peptide entry inhibitors and methods of determining such inhibitors that are bindable to regions of the dengue virus E protein, as candidates for in vivo anti-viral compounds.

BACKGROUND OF THE INVENTION

Dengue virus, a member of the flavivirus family, imposes one of the largest social and economic burdens of any mosquito-borne viral pathogen. There is no specific treatment for infection, and control of dengue virus by vaccination has proved elusive. Several other flaviviruses are important human pathogens, including yellow fever, West Nile, tick-borne encephalitis (TBE) and Japanese encephalitis viruses (JE).

Enveloped viruses enter cells by membrane fusion. Structural protein E of the flavivirus, which mediates both receptor binding and fusion, is a so-called "class II" viral fusion protein. Two classes of viral "fusion machines" have been identified so far. Class I viral fusion proteins include those of the myxo- and paramyxoviruses (e.g., influenza), the retroviruses (e.g., HIV), and the filoviruses (e.g., Ebola). Class II fusion proteins are found in not only the flaviviruses (yellow fever, West Nile, etc.), but also the alphaviruses which includes Semliki Forest virus and Sindbis virus, as well as Hepatitis C. The structural characteristics of the two classes are quite different, but both accomplish the same task, i.e. fusion of two lipid bilayers.

The more familiar class I fusion proteins, exemplified by the haemagglutinin (HA) of influenza virus and gp120/gp41 of HIV, have a "fusion peptide" at or near the N-terminus of an internal cleavage point. This hydrophobic and glycine-rich segment, buried in the cleaved-primed trimer of the class I fusion protein, emerges when a large-scale conformational rearrangement is triggered by low pH (in the case of HA), receptor binding (in the case of gp120/gp41), or other cell-entry related signal. The likely sequence of events that follow include an interaction of the fusion peptide with the target-cell membrane and a refolding of the trimer. The latter step brings together the fusion peptide and viral-membrane anchor, thereby drawing together the cellular and viral membranes and initiating the bilayer fusion process.

The class II proteins, found so far in flaviviruses and alphaviruses, have evolved structurally different but mechanistically related fusion architecture. As in class I proteins, a proteolytic cleavage (of PrM to M in flaviviruses, or of pE2 to E2 in alphaviruses) yields mature virions, with the fusion proteins in a metastable conformation, primed for fusion. The fusion peptide, an internal loop at the tip of an elongated subdomain of the protein, is buried at a protein interface and becomes exposed in the conformational change initiated by exposure to low pH.

The mechanism of fusion of class II viral fusion proteins is not well-understood, and there are no therapeutics that can specifically inhibit the fusion of such proteins. Only the prefusion structures of one flaviviral and one alphaviral envelope protein have been determined to date. There is a need for entry inhibitors that can specifically inhibit viral infection by flaviviruses, alphaviruses, and hepatitis viruses. Further, because fusion is a key step in viral infectivity, a better understanding of the mechanism of class II envelope proteins, including the dengue virus envelope protein, and identification of druggable regions within such proteins will further development of therapeutics that can specifically inhibit viral infection by flaviviruses, alphaviruses, and hepatitis viruses.

SUMMARY OF THE INVENTION

The invention provides peptide entry inhibitors that are bindable to regions in viral class II E proteins. The interaction of an inhibitor with such regions, or the modulation of the activity of such regions with an inhibitor, could inhibit viral fusion and hence viral infectivity. In one aspect, the invention provides compounds and methods of screening the compounds against these bindable regions in order to discover therapeutic candidates for a disease caused by a virus having a class II protein. Diseases for which a therapeutic candidate may be screened include dengue fever, dengue hemorrhagic fever, tick-borne encephalitis, West Nile virus disease, yellow fever and hepatitis C.

In one embodiment, a method for identifying a therapeutic candidate for a disease caused by a virus having class II E protein, comprises contacting a class II E protein which comprises a bindable region with a compound, wherein binding of said compound indicates a therapeutic candidate. Compounds may be selected from compounds including peptides. Binding may be assayed either in vitro or in vivo. In certain embodiments, the protein is dengue virus E protein. Such bindable regions also may be utilized in the structure determination, drug screening, drug design, and other methods described and claimed herein.

Furthermore, the invention provides for methods of inhibiting viral infection by dengue virus and/or binding between the virion envelope of dengue viruses and membranes of the target cell (the process that delivers the viral genome into the cell cytoplasm). The invention provides for methods that employ peptides or peptide derivatives to inhibit dengue virus:cell binding. The invention provides for methods of treatment of diseases induced by the dengue virus.

In another embodiment of the invention, a peptide entry inhibitor includes an amino acid sequence presented as SEQ ID NO: 1.

In yet another embodiment of the invention, a method for determining an inhibitor for a virus includes the steps of contacting a peptide within a bindable region of the virus, and determining the bindability of the compound to the bindable region of virus, wherein the bindability of compound measures inhibitory activity of the compound against the virus.

In still yet another embodiment of the invention, a method of treatment of dengue virus infection includes the steps of administering a therapeutically effective amount of a peptide, wherein the peptide has an amino acid sequence presented as SEQ ID NO: 1.

DETAILED DESCRIPTION OF THE INVENTION

An embodiment of the invention relates to methods of inhibiting dengue infection that includes inhibiting the fusion between the virion envelope and a cell membrane, the process that delivers the viral genome into the cell cytoplasm.

Figure 1:
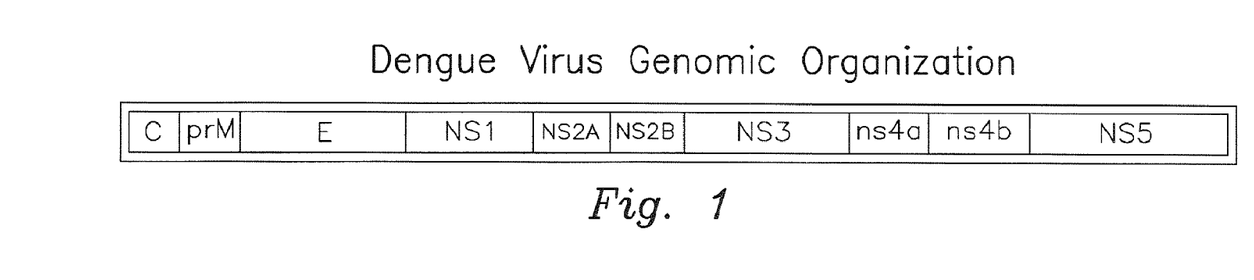
FIG. 1 illustrates the genomic organization of the dengue virus.

Any peptide or protein which inhibits the fusion between the dengue virion envelope and a cell membrane, including those of the dengue virus which infect human as well as nonhuman hosts, may be used according to the invention. In various embodiments of the invention, these dengue peptide entry inhibitors may include, but are not limited to peptides related to several membrane-interactive bindable regions of dengue virus proteins. The genomic organization of the dengue virus is illustrated in FIG. 1.

The term "bindable region", when used in reference to a peptide, nucleic acid, complex and the like, refers to a region of a dengue virus E protein or other class II E protein which is a target or is a likely target for binding an agent that reduces or inhibits viral infectivity. For a peptide, a bindable region generally refers to a region wherein several amino acids of a peptide would be capable of interacting with at least a portion of the dengue virus E protein. For a peptide or complex thereof, bindable regions including binding pockets and sites, interfaces between domains of a peptide or complex, surface grooves or contours or surfaces of a peptide or complex which are capable of participating in interactions with another molecule, such as a cell membrane.

In one embodiment, the dengue peptide entry inhibitor is DN81 having a SEQ ID No. 1: RWMVWRHWFHRLR-LPYNPGKNKQNQQWP.

In another embodiment of the invention, peptides related to the dengue peptide entry inhibitor include homologous peptides. As used herein, the term homologous dengue peptide entry inhibitors is to be interpreted as peptides having a sequence identical to the corresponding portion of the dengue virus inhibitory protein and peptides in which one or more amino acids are substituted by functionally equivalent amino acids. The term also refers to derivatives of these peptides, including but not limited to benzylated derivatives, glycosylated derivatives, and peptides which include enantiomers of naturally occurring amino acids.

In other embodiments of the invention, the dengue peptide entry inhibitors, related peptides or derivatives are linked to a carrier molecule such as a protein. Proteins contemplated as being useful according to this embodiment of the invention, include but are not limited to, human serum albumen. Dengue peptide entry inhibitors comprising additional amino acids are also contemplated as useful according to the invention.

The dengue entry inhibitory peptides of the invention may be utilized to inhibit dengue virus virion:cell fusion and may, accordingly, be used in the treatment of dengue virus infection in mammals. These mammals are patients that may include, but are not limited to, humans, dogs, cats, birds, horses, etc. The peptides of the invention may be administered to patients in any sterile, biocompatible pharmaceutical carrier, including, but not limited to, saline, buffered saline, dextrose, and water. Methods for administering peptides to patients are well known to those of skill in the art; they include, but are not limited to, intradermal, intramuscular, intraperitoneal, intravenous, subcutaneous, oral, and intranasal. In addition, it may be desirable to introduce the pharmaceutical compositions of the invention into the central nervous system by any suitable route, including intravenous injection. Other embodiments contemplate the administration of the dengue entry inhibitory peptides or derivatives thereof, linked to a molecular carrier including human serum albumin (HSA).

A number of techniques can be used to screen, identify, select and design chemical entities capable of associating with a dengue virus E protein or other class II E protein, structurally homologous molecules, and other molecules. Knowledge of the structure for a dengue virus E protein or other class II E protein, determined in accordance with the methods described herein, permits the design and/or identification of molecules and/or other modulators which have a shape complementary to the conformation of a dengue virus E protein or other class II E protein, or more particularly, a druggable region thereof. It is understood that such techniques and methods may use, in addition to the exact structural coordinates and other information for a dengue virus E protein or other class II E protein, and structural equivalents thereof.

In one aspect, the method of drug design generally includes computationally evaluating the potential of a selected chemical compound to associate with a molecule or complex, for example any class II viral E protein. For example, this method may include the steps of employing computational means to perform a fitting operation between the selected chemical compound and a bindable region of the molecule or complex and analyzing the results of the fitting operation to quantify the association between the chemical entity and the bindable region.

In another aspect, candidates as dengue peptide entry inhibitors of DENV infectivity that target the viral E protein were determined through the use of primary amino acid sequence data in conjunction a Monte Carlo binding algorithm and a Wimley-White interfacial hydrophobicity scale.

The term "Monte Carlo," as used herein, generally refers to any reasonably random or quasi-random procedure for generating values of allowed variables. Examples of Monte Carlo methods include choosing values: (a) randomly from allowed values; (b) via a quasi-random sequence like LDS (Low Discrepancy Sequence); (c) randomly, but biased with experimental or theoretical a priori information; and (d) from a non-trivial distribution via a Markov sequence.

More particularly, a "Monte Carlo" method is a technique which obtains a probabilistic approximation to the solution of a problem by using statistical sampling techniques. One Monte Carlo method is a Markov process, i.e., a series of random events in which the probability of an occurrence of each event depends only on the immediately preceding outcome. (See Kalos, M. H. and Whitlock, P. A. "Monte Carlo Methods: Volume I: Basics," John Wiley & Sons, New York, 1986; and Frenkel, D., and Smit, B. "Understanding Molecular Simulation: From Algorithms to Applications: Academic Press, San Diego, 1996).

The Wimley-White interfacial hydrophobicity scale is a tool for exploring the topology and other features of membrane proteins by means of hydropathy plots based upon thermodynamic principles.

Materials and Methods

Preparation of Dengue Peptide Entry Inhibitors

Peptides may be produced from naturally occurring or recombinant viral proteins, or may be produced using standard recombinant DNA techniques (e.g. the expression of peptide by a microorganism which contains recombinant nucleic acid molecule encoding the desired peptide, under the control of a suitable transcriptional promoter, and the harvesting of desired peptide from said microorganism). Preferably, the peptides of the invention may be synthesized using any methodology known in the art, including but not limited to, Merrifield solid phase synthesis (Clark-Lewis et al., 1986, Science 231:134-139).

Viruses and Cells

DENV-1 strain HI-1, DENV-2 strain NG-2, DENV-3 strain H-78, and DENV-4 strain H-42 were obtained from R. Tesh at the World Health Organization Arbovirus Reference Laboratory at the University of Texas at Galveston. Viruses were propagated in the African green monkey kidney epithelial cell line, LLCMK-2, a gift of K. Olsen at Colorado State University. LLCMK-2 cells were grown in Dulbecco's modified eagle medium (DMEM) with 10% (v/v) fetal bovine serum (FBS), 2 mM Glutamax, 100 U/ml penicillin G, 100 µg/ml streptomycin and 0.25 µg/ml amphotericin B, at 37° C. with 5% (v/v) $CO_2$.

Focus Forming Unit (FFU) Reduction Assay

LLCMK-2 target cells were seeded at a density of $1 \times 10^5$ cells in each well of a E-well plate 24 h prior to infection. Approximately 200 FFU of virus were incubated with or without chemistries in serum-free DMEM for 1 h at rt. Virus/chemistry or virus/control mixtures were allowed to infect confluent target cell monolayers for 1 h at 37° C., with rocking every 15 m, after which time the medium was aspirated and overlaid with fresh DMEM/10% (v/v) FBS containing 0.85% (w/v) Sea-Plaque Agarose (Cambrex Bio Science, Rockland, Me.). Cells with agar overlays were incubated at 4° C. for 20 m to set the agar. Infected cells were then incubated at 37° C. with 5% $CO_2$ for 3 days (DENY-1, 3 and 4) or 5 days (DENV-2). Infected cultures were fixed with 10% formalin overnight at 4° C., permeablized with 70% (v/v) ethanol for 20 m, and rinsed with PBS prior to immunostaining. Virus foci were detected using supernatant from mouse anti-DENV hybridoma E60 (obtained from M. Diamond at Washington University) followed by horseradish peroxidase-conjugated goat anti-mouse immunoglobulin (Pierce, Rockford, Ill.) and developed using AEC chromogen substrate (Dako, Carpinteria, Calif.). Results were expressed as the average of at least two independent trials with three replicates in each trial.

Cytoxicity Assay

The cytotoxicity of the chemistries was measured by monitoring mitochondrial reductase activity using the TACS™ MTT cell proliferation assay (R&D Systems, Inc., Minneapolis, Minn.) according to the manufacturer's instructions. Dilutions of chemistries in serum-free DMEM were added to confluent monolayers of LLCMK-2 cells in 96-well plates for 1 h at 37° C., similar to the focus forming inhibition assays, and subsequently incubated at 37° C. with 5% (v/v) $CO_2$ for 24 h. Absorbance at 560 nm was measured using a Tecan GeniosPro plate reader (Tecan US, Durham, N.C.).

Mechanistic Assays with DN81

Post-Entry Focus-Forming Assay with DN81 Against DENV-2

To determine if the observed inhibitory effect was due to interference with post-entry steps in the viral life cycle, approximately 200 FFU of DENV-2 without DN81 was allowed to bind and enter target cells for 1 h at 37° C. as described for the focus forming assay. Unbound virus was then removed by rinsing with PBS and DN81 was added to the cells post-entry for 1 hr at 37° C. Cultures were washed again in PBS and agarose overlays, incubation, and immunological detection was conducted as described for the focus forming assay.

Pre-Binding Focus-Forming Assay with DN81 Against DENV-2

To determine if the observed inhibitory effect was due to interference caused by modifications to the target cell surface, DN81 was incubated with the target cells for 1 h at 4° C., the cells were rinsed with PBS, and approximately 200 FFU of DENV-2 was allowed to infect the cells at 4° C. Agarose overlays, incubation, and immunological detection were conducted as described for the focus forming assay.

Post-Binding Focus-Forming Assay with DN81 Against DENV-2

To determine if the observed inhibitory effect was due to interference with interactions that occur pre-binding versus post-binding of virions to the target cells, approximately 200 FFU of DENV-2 was allowed to bind to target LLCMK-2 cells for 1 h at 4° C. to allow binding, but prevent internalization. Unbound virus was washed off with PBS at 4° C., then CF 238 was added and incubated at 4° C. for 1 h. Cultures were washed again in 4° C. PBS and warmed to 37° C. Agarose overlays, incubation, and immunological detection were conducted as described for the focus forming assay.

qRT-PCR Virus Binding Assay

Infection of LLCMK-2 target cells in six well plates was performed in duplicate using $10^5$ FFU of DENV-2 that had been pre-incubated for 45 m at 4° C. with CF 238 or pooled heterotypic anti-DENV human serum. After a 45 m infection at 4° C., infected monolayers were washed with PBS and harvested with a cell scraper, added to a 1.5 ml microfuge tube containing 350 µl of AR-200 silicone oil (Sigma-Aldrich, St. Louis, Mo.) mixed with 150 µl of silicone fluid (Thomas, Swedesboro, N.J.), and spun at 14,000 rpm in a microfuge for 1 m to separate the unbound virus from the cell-bound virus in the pellets. The tubes were then submerged in liquid nitrogen for 30 s to freeze the contents. The cell pellets with bound virus were recovered by clipping off the bottoms of the tubes with small wire clippers into 15 ml conical tubes. Viral RNA was extracted from the cell pellets using the Qiagen Viral RNA Extraction kit (Qiagen, Chatsworth, Calif.).

Quantitative real time reverse transcription PCR (qRT-PCR) was performed on the extracted RNA using the Quantitect Sybr Green RT-PCR kit (Qiagen inc., Chatsworth, Calif.), following the manufacturer's specifications and amplification protocols, using dengue-specific primers: (Den2F: catatgggtggaatctagtacg, Den2R: catatgggtg-gaatctagtacg). Each reaction was performed in 20 µL total volume (10 µL 2×SYBR green master mix, 0.5 µL of 10 µM of each primer, 0.2 µL reverse transcriptase, and 5 µL viral RNA) using a Lightcycler thermal cycler (Roche Diagnostics, Carlsbad, Calif.), and according to the following amplification protocol: 50° C. for 20 min to reverse transcribe the RNA; 95° C. for 15 min to activate the HotStart Taq DNA Polymerase; 45 PCR cycles: 94° C. for 15 s, 50° C. for 15 s, 72° C. for 30 s, the last step was also the fluorescence data acquisition step. Melting curve analysis was performed by a slow increase in temperature (0.1° C./s) up to 95° C. The threshold cycle, representing the number of cycles at which the fluorescence of the amplified product was significantly above background, was calculated using Lightcycler 5.3.2 software (Roche).

Analysis

Figures were generated using the Origin 6.0 graphing software (Northampton, Mass.). Statistical analyses were performed using the Graphpad Prism 4.0 software package (San Diego, Calif.). P values less than 0.05 were considered significant.

Results

Inhibition Assays with Different Chemistries Against DENV-2

Figure 2:
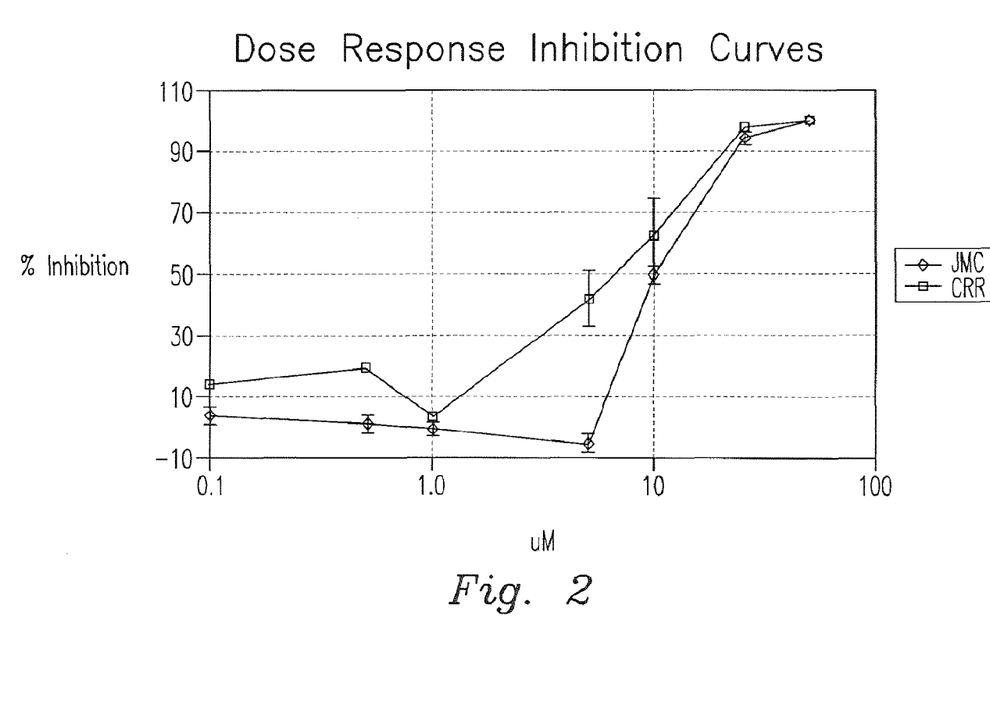
FIG. 2 is a graph representing the dose response inhibition curve against DENV-2 for the DN81 peptide.
Figure 3:
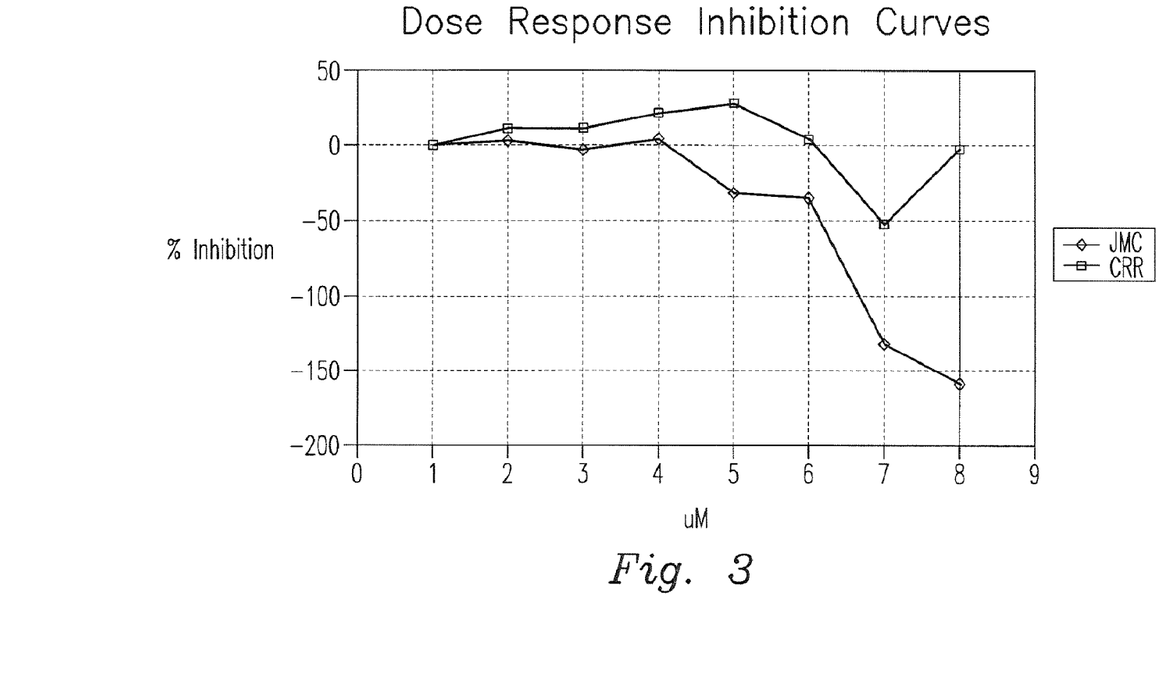
FIG. 3 is a graph representing the dose response inhibition curve against DENV-2 for a scrambled sequence for the DN81 peptide.

Focus-forming assays were used to quantitate the inhibitory activities of each chemistry against DENV-2 as previously described (Hrobowski, et al, 2005). As seen in FIG. 2, dose response curves were generated over concentration ranges dictated by the solubilities of the chemistries in 1% DMSO/aqueous solution. Control 1% DMSO/PBS solutions showed no DENV inhibitory activity in this assay system (data not shown). The DN81 peptide showed an increase in inhibitory activity as a function of concentration. As seen in FIG. 3, a scrambled sequence of the 10AN peptide showed no consistent activity directed towards inhibition against DENV-2.

Cytotoxicity

Figure 4:
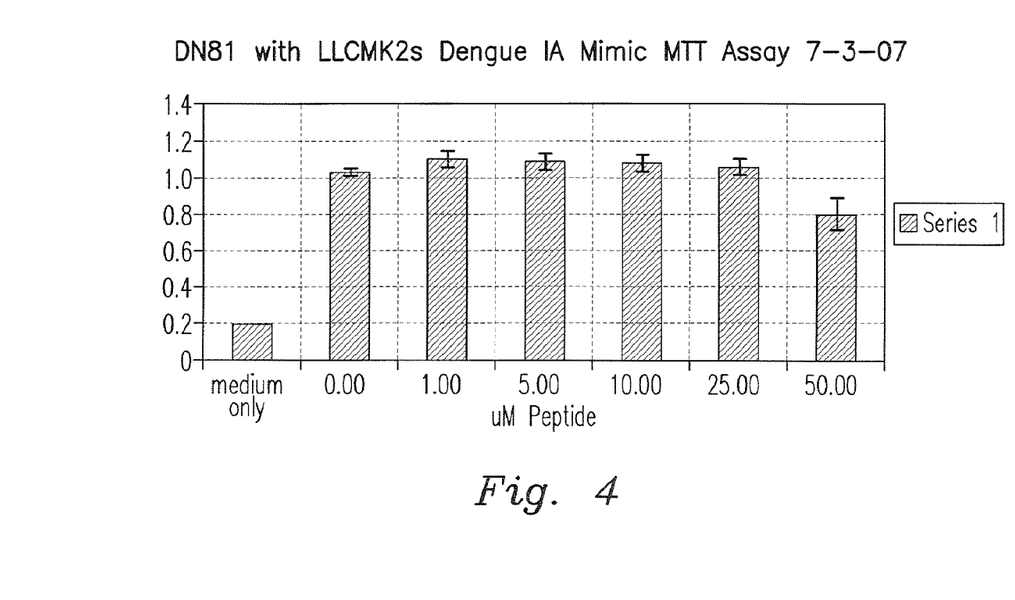
FIG. 4 is a graph representing the cytotoxicity assay of the DN81 peptide at various concentrations.

To determine if the observed DENV inhibition effects were due to cellular toxicity that impacted viral replication, the effect of the chemistry on the mitochondrial reductase activity of the target cells was measured over the concentration ranges that showed viral inhibition. In confluent cell monolayers that replicated the conditions in the focus forming assays no sign of toxicity was observed with any compound compared to medium only controls (p>0.05, ANOVA with Dunnett's posthoc test) as seen in FIG. 4. Thus, the inhibitory activity of the DN81 peptide is not due to toxicity.

Pre-Binding Focus-Forming Assay with DN81 Against DENV-2

In this assay, DN81 was added to target cells for 1 h prior to infection with DENV-2 to determine if DN81 inhibits entry through interaction directly with the target cells. Treatment of target cells with DN81 prior to DENV-2 infection resulted in no evidence of inhibition, indicating that DN81 does not function by interacting with or modifying the target cell surface, and must be present along with the virus in order to inhibit entry.

qRT-PCR Virus Binding Assay with DN81 Against DENV-2

In order to directly test if DN81 interferes with virus binding to target cells, binding assays were conducted using qRT-PCR to monitor attachment of virus to target cells. In these experiments, virus was co-incubated with DN81 for 45 m at 4° C. and used to infect target cells at 4° C. for 45 m. The cells were then scraped off the plates and centrifuged through an oil mixture with a density that allowed passage of the cells, but not free virus, to the bottom of the tube. RNA was then extracted from the cell pellets and amplified with DENV-2 specific primers. Pre-incubation of DENV-2 with DN81 did not inhibit virus binding, as measured by the qRT-PCR signal, whereas pre-incubation of DENV-2 with pooled human heterotypic anti-DENV-2 serum resulted in a large decrease in the attachment of virus to target cells. This indicates that DN81 does not prevent virus binding/attachment to target cells under the experimental condition tested.

Based upon the foregoing disclosure, it should now be apparent that the use of peptide entry inhibitors that are bindable to regions of the dengue virus E protein, as potential candidates for the development of anti-viral compounds as described herein will carry out the objects set forth hereinabove. It is, therefore, to be understood that any variations evident fall within the scope of the claimed invention and thus, the selection of specific component elements can be determined without departing from the spirit of the invention herein disclosed and described.

---

---

What is claimed is:

1. A synthetic peptide comprising: an amino acid sequence presented as SEQ ID NO: 1.

2. The peptide of claim 1, wherein the peptide inhibits a class II viral envelope protein.

3. The peptide of claim 2, wherein the class II envelope protein is a dengue virus E protein.

4. The peptide of claim 1, wherein the peptide inhibits dengue virus virion:cell fusion.

5. A pharmaceutical composition comprising the peptide of claim 1.

6. The pharmaceutical composition of claim 5, further comprising a biocompatible carrier.

7. The pharmaceutical composition of claim 6, wherein the biocompatible carrier is selected from the group consisting of saline, buffered saline, dextrose and water.

8. A method of treating dengue virus infection in a subject comprising the steps of: administering a therapeutically effective amount of the peptide comprising the amino acid sequence presented as SEQ ID NO: 1 to a subject in need thereof.

9. The method of claim 8, wherein the peptide inhibits dengue virus virion:cell fusion.

10. The method of claim 8, wherein the peptide is administered intradermally, intramuscularly, intraperitoneally, intravenously, subcutaneously, orally or intranasally.

11. The method of claim 8, wherein the peptide is conjugated to a carrier molecule.

12. The method of claim 11, wherein the carrier molecule is human serum albumin (HSA).

13. The method of claim 10, wherein the peptide is administered to a mammal.

* * * * *

UNITED STATES PATENT AND TRADEMARK OFFICE
CERTIFICATE OF CORRECTION

| | | |
|---|---|---|
| PATENT NO. | : 8,541,377 B2 | Page 1 of 1 |
| APPLICATION NO. | : 12/668828 | |
| DATED | : September 24, 2013 | |
| INVENTOR(S) | : Scott F. Michael et al. | |

It is certified that error appears in the above-identified patent and that said Letters Patent is hereby corrected as shown below:

In the Specification

Column 1, Lines 15-19 should read:

This invention was made with government support under GM068152, awarded by the National Institutes of Health. The government has certain rights in the invention.

Signed and Sealed this
Twenty-sixth Day of May, 2015

Michelle K. Lee
*Director of the United States Patent and Trademark Office*

SEQUENCE LISTING

```
<160> NUMBER OF SEQ ID NOS: 1

<210> SEQ ID NO 1
<211> LENGTH: 28
<212> TYPE: PRT
<213> ORGANISM: Artificial
<220> FEATURE:
<223> OTHER INFORMATION: Artificially synthesized polypeptide

<400> SEQUENCE: 1

Arg Trp Met Val Trp Arg His Trp Phe His Arg Leu Arg Leu Pro Tyr
1               5                   10                  15

Asn Pro Gly Lys Asn Lys Gln Asn Gln Gln Trp Pro
            20                  25
```